United States Patent
Köhler

(10) Patent No.: US 6,792,362 B2
(45) Date of Patent: Sep. 14, 2004

(54) APPARATUS FOR DETERMINING THE MOISTURE CONTENT OF A MEDIUM

(75) Inventor: Kurt Köhler, Ettlingen (DE)

(73) Assignee: imko Intelligente Micromodule Köhler GmbH, Ettlingen (DE)

(*) Notice: Subject to any disclaimer, the term of this patent is extended or adjusted under 35 U.S.C. 154(b) by 0 days.

(21) Appl. No.: 10/394,374

(22) Filed: Mar. 21, 2003

(65) Prior Publication Data
US 2003/0191588 A1 Oct. 9, 2003

(30) Foreign Application Priority Data
Apr. 5, 2002 (DE) .................. 202 05 302 U

(51) Int. Cl.⁷ .................. G06F 19/00; G01R 31/11; G01R 27/26
(52) U.S. Cl. .................. 702/50; 702/55; 324/664; 324/533
(58) Field of Search .................. 702/50, 55; 324/525, 324/532–535, 643, 663–664, 694, 710

(56) References Cited

U.S. PATENT DOCUMENTS 5,212,453 A * 5/1993 Koehler et al. ............ 324/664
5,488,312 A * 1/1996 Havener et al. ............ 324/689
5,663,650 A 9/1997 McMahon .................. 324/670
5,898,308 A * 4/1999 Champion .................. 324/643
6,025,724 A * 2/2000 Moshe et al. ............... 324/640

FOREIGN PATENT DOCUMENTS

EP 0 232 566 8/1987
GB 2 210 693 6/1989

* cited by examiner

Primary Examiner—John Barlow
Assistant Examiner—Meagan Walling
(74) Attorney, Agent, or Firm—Klaus J. Bach

(57) ABSTRACT

In an apparatus for determining the moisture content of a medium forming a dielectric of a measuring conduit of a probe, which apparatus includes an electronic evaluation unit, a signal generator providing a pulse signal to one end of the measuring conduit, a receiver for receiving a reflected signal returned to the one end of the measuring conduit and a time measuring device for determining the time elapsed between the supply of the signal and the return of the reflected signal, the electronic evaluation unit is arranged in close proximity to the one end of the measuring conduit and provided with temperature compensating means.

5 Claims, 1 Drawing Sheet

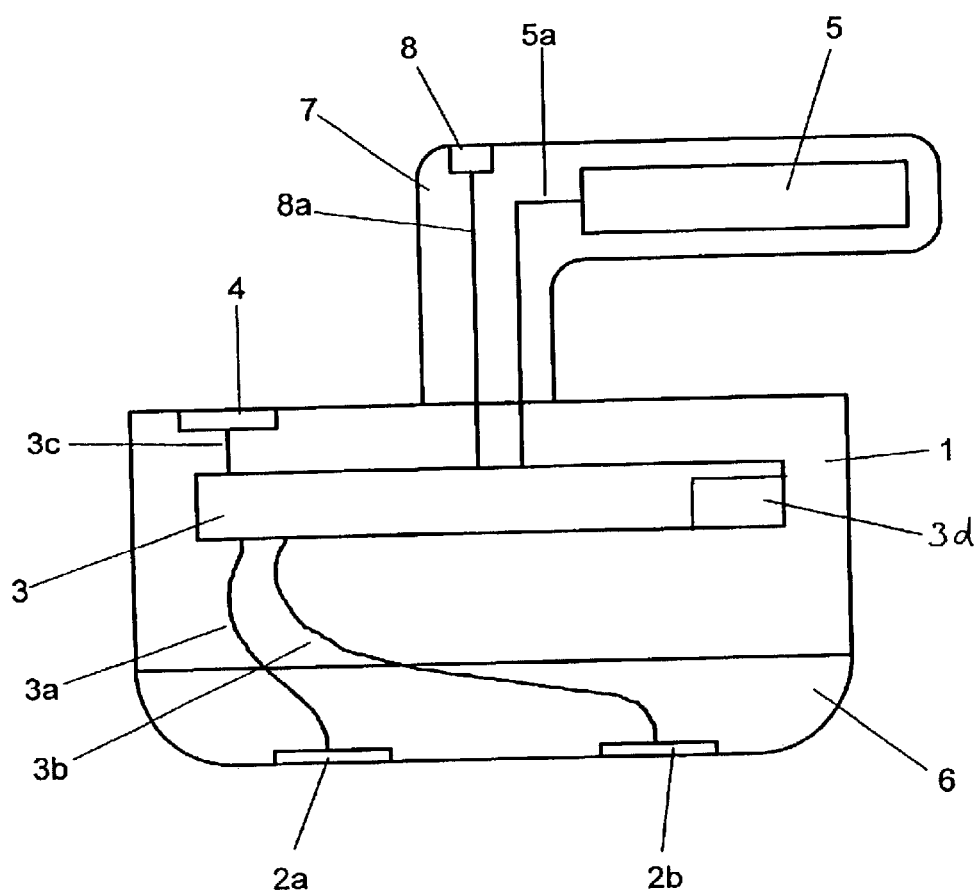

APPARATUS FOR DETERMINING THE MOISTURE CONTENT OF A MEDIUM

BACKGROUND OF THE INVENTION

The invention resides in an apparatus for determining the moisture content of a medium, which forms the dielectric of a measuring conduit representing a probe. The apparatus includes an electronic evaluation device with a pulse signal generator supplying a pulse signal to one end of the measuring conduit, a receiver receiving the reflected signal at the same end and a device for determining the time delay between the sent signal the reflected signal.

Such an apparatus is known for example from EP 0 478 851 B1 and has been successfully commercialized by the patentee. The essential element of the known apparatus is the measuring cable.

The measuring conduit can have different forms. The measuring conduit may consist for example of two parallel rods or it may be in the form of a probe as disclosed in DE 43 34 649 C2.

The probe disclosed in DE 43 34 649 C2 comprises a cylindrical body on which the measuring conduit is disposed. The probe body may also be shaped differently depending on requirements. For example, the body may be triangular in cross-section, square, hexagonal or oval. The body may furthermore be solid or hollow. However, it always includes on its surface electrical conductors arranged in spaced relationship and forming the measuring conduit.

In the known apparatus, the probe is connected to the electronic evaluation unit by way of a coaxial cable. With the use of a co-axial cable as connecting means, errors introduced by the connecting means can be kept relatively small. But, it is still desirable to increase the accuracy of the apparatus.

It is the object of the present invention to provide an apparatus for determining the moisture content of a medium which apparatus has a higher accuracy than those referred to above.

SUMMARY OF THE INVENTION

In an apparatus for determining the moisture content of a medium forming a dielectric of a measuring conduit of a probe, which apparatus includes an electronic evaluation unit, a signal generator providing a pulse signal to one end of the measuring conduit, a receiver for receiving a reflected signal returned to the one end of the measuring conduit and a time measuring device for determining the time elapsed between the supply of the signal and the return of the reflected signal, the electronic evaluation unit is arranged in close proximity to the one end of the measuring conduit and provided with temperature compensating means.

Since the electronic evaluation unit includes an arrangement for temperature compensation and is arranged directly at the end of the measuring conduit a substantially greater accuracy can be achieved. Although, in the past, an arrangement of the evaluation unit at the end of the measuring conduit and a temperature compensation are provided only for a relatively small accuracy improvement, it has surprisingly been found that a combination of a temperature compensation with the arrangement of the electronic evaluation unit directly at the end of the measuring conduit provides for a substantial improvement of the accuracy of the apparatus. The systematic error inherent in the known apparatus could be reduced with the arrangement according to the invention essentially to zero.

An embodiment of the invention, wherein the electronic evaluation unit is disposed in a probe housing has been found to be particularly advantageous. With the arrangement of the electronic evaluation unit within the probe housing, the electronic evaluation unit is not only arranged directly at the end of the measuring conduit but, furthermore, the apparatus is very compact and also very easy to use.

It is in this connection particularly advantageous, if the temperature compensation means is also arranged in the probe housing. In this way, the temperature of the measuring conduit can be compensated for together with the temperature of the electronic evaluation unit.

It is very advantageous if the temperature compensation means includes a storage, in which a first reference measurement value of a predetermined material moisture content at a first temperature of the apparatus or, respectively, the electronic evaluation unit and a second measurement reference value of the predetermined material moisture content at a second temperature of the apparatus or, respectively, the electronic evaluation unit is stored. It is particularly advantageous if the reference measurement values are determined individually for each apparatus manufactured. With the reference measurement values, the changes of a measurement value over the temperature between the first and second temperature can easily be determined by interpolation. When, during later operation, a moisture content value determined in a measurement is corrected with the temperature-dependent adjustments determined in this way, the measurement value becomes highly accurate.

An embodiment of the invention wherein the measurement conduit is arranged at the surface of the probe housing and, in this area, the surface includes a pillow filled with gel has also been found to be advantageous. Then the measuring conduit can be very easily placed onto the medium to be measured. With the gel-filled pillow the probe can be placed onto the surface of the medium to be measured in a very gentle manner.

In another embodiment of the invention, electric power is supplied by an energy storage device also arranged in the probe housing. In this way, handling of the apparatus is further substantially facilitated.

It has also been found to be advantageous if the probe housing includes indicating means. With such indicating means in the probe housing use of the apparatus is facilitated.

Furthermore, the probe housing may include a handle with switch buttons for starting a measurement procedure. Then the apparatus can be handled with one hand.

Further particulars, features and advantages of the present invention will be described below on the basis of the accompanying drawing.

BRIEF DESCRIPTION OF THE DRAWINGS

The sole FIGURE shows schematically an arrangement according to the invention.

DESCRIPTION OF A PREFERRED EMBODIMENT

As shown in the FIGURE, a probe includes a cylindrical housing 1, which is provided at its front end with a pillow 6 filled with gel. At the opposite end, the housing 1 is provided with a handle 7.

In the gel-filled pillow 6, two electrical conduits 2a, 2b are arranged in spaced parallel relationship. They are connected to an evaluation device 3 by connecting wires 3a, 3b. The connecting wires 3a, 3b are fixed in the housing 1 so that their length remains unchanged.

The handle 7 includes a contactor 8, which is connected to the electronic evaluation unit 3 by a connecting cable 8a. By means of the contactor 8, the measuring procedure of the apparatus can be initiated.

The probe housing 1 further includes an indicator 4, which is connected to the electronic evaluation unit 3 by a cable 3c. The electronic evaluation unit 3 is further connected by an energy supply cable 5a to an energy storage device 5, which is also arranged in the housing 1. The energy storage device 5 may be a rechargeable battery.

The electronic evaluation unit 3 includes a signal generator which supplies a pulse-signal to one end of the measuring conduits 2a, 2b and also a receiver, which receives the reflected signals returning to the same end of the measuring conductors. Furthermore, the electronic evaluation device 3 includes a device for measuring the time elapsed between the supply of a signal pulse to the measuring conductor and the return of the reflection signal. In addition, the electronic measuring device includes a temperature compensation means.

The electronic evaluation unit 3 further includes a storage 3d, in which a first reference measurement value for a predetermined material moisture content at a first temperature of the apparatus and a second reference measurement value of the predetermined material moisture content at a second temperature of the apparatus are stored. For determining the first reference measurement value, the apparatus, or at least the electronic evaluation unit 3, is brought to a temperature of, for example, 23° C. and the moisture content of a medium with a predetermined moisture content is measured by the apparatus. Then the apparatus or, respectively, the electronic evaluation unit 3 is heated for example to 53° C. and the material moisture content of the same medium with the same moisture content is determined. The reference values determined in this way are stored in the storage 3d.

By a comparing the two reference measurement values, the temperature behavior of the apparatus or respectively the evaluation unit 3 is obtained. By linear interpolation, the change of the measurement value over the temperature between the second and the first temperatures can be determined. If, for example, during operation of the apparatus, a measurement is performed with the apparatus being at 38° C., the measured moisture content is corrected by half the difference of the two reference measurement values. In this way, the temperature influences on the apparatus can be almost completely corrected.

With the evaluation unit arranged in the probe housing 3 and being connected by connecting wires 3a, 3b directly to the measuring conduits 2a, 2b and further is provided with temperatures compensation means the accuracy of the moisture content determining apparatus according to the invention has been found to be very accurate.

What is claimed is:

1. An apparatus for determining the moisture content of a medium forming a dielectric of a measuring conduit of a probe said apparatus including an electronic evaluation unit, a signal generator providing a pulse signal to one end of said measuring conduit, a receiver for receiving a reflected signal returned to said one end of the measuring conduit, and a time measuring device for determining the time elapsed between the supply of said signal to said measuring conduit and the return of the reflected signal to the one end of the measuring conduit, said evaluation unit being arranged within a housing to which also said measuring conduit is connected so as to be in a close predetermined proximity to the one end of said measuring conduit, said housing with said evaluation unit including temperature compensating means.

2. An apparatus according to claim 1, wherein said temperature compensating means includes a storage in which a first reference value of a predetermined material moisture content at a first temperature of the electronic evaluation device and a second reference value of the predetermined material moisture content at a second temperature of the electronic evaluation device are stored.

3. An apparatus according to claim 1, wherein gel-filled pillow is disposed on a surface of said probe housing and said measuring conduit is disposed adjacent the surface of said gel-filled pillow.

4. An apparatus according to claim 1, wherein said housing includes an electric energy storage device providing electric power to said apparatus.

5. An apparatus according to claim 1, wherein said housing includes a handle provided with a contactor for initiating a measuring procedure.

* * * * *